(12) United States Patent
Prager et al.

(10) Patent No.: US 8,372,085 B2
(45) Date of Patent: Feb. 12, 2013

(54) SCREWDRIVER FOR BONE SCREWS

(75) Inventors: Ronald Prager, Bovenau (DE); Stefan Völzow, Mönckeberg (DE)

(73) Assignee: Stryker Trauma GmbH (DE)

( * ) Notice: Subject to any disclaimer, the term of this patent is extended or adjusted under 35 U.S.C. 154(b) by 1335 days.

(21) Appl. No.: 12/148,324

(22) Filed: Apr. 18, 2008

(65) Prior Publication Data

US 2008/0243136 A1  Oct. 2, 2008

Related U.S. Application Data

(63) Continuation of application No. 10/990,243, filed on Nov. 16, 2004, now abandoned.

(30) Foreign Application Priority Data

Nov. 24, 2003  (DE) .............................. 203 18 263 U
Nov. 25, 2003  (DE) .............................. 203 18 703 U

(51) Int. Cl.
*A61B 17/58* (2006.01)
(52) U.S. Cl. ...................................................... 606/104
(58) Field of Classification Search ............. 606/79–81, 606/86 R, 104; 81/64, 177.6
See application file for complete search history.

(56) References Cited

U.S. PATENT DOCUMENTS

| | | | |
|---|---|---|---|
| 1,507,990 A | | 9/1924 | Donaldson |
| 1,653,995 A | * | 12/1927 | English ............................ 81/8.1 |
| 2,796,101 A | | 6/1957 | Hasemann et al. |
| 2,814,322 A | | 11/1957 | Kupfrian |
| 3,585,885 A | | 6/1971 | Carr |
| 4,876,929 A | | 10/1989 | Kozak |
| 5,464,407 A | | 11/1995 | McGuire |
| 5,527,316 A | | 6/1996 | Stone et al. |
| 5,572,913 A | * | 11/1996 | Nasiell ........................ 81/177.6 |
| 5,638,726 A | * | 6/1997 | Pelkonen et al. ............ 81/57.43 |
| 5,797,918 A | | 8/1998 | McGuire et al. |
| 5,941,139 A | | 8/1999 | Vodehnal |
| 6,164,169 A | | 12/2000 | Goff |
| 6,179,532 B1 | | 1/2001 | Oldham |
| 6,337,142 B2 | | 1/2002 | Harder et al. |
| 6,684,770 B2 | | 2/2004 | Kamen et al. |
| 2005/0216027 A1 | | 9/2005 | Suh et al. |

* cited by examiner

*Primary Examiner* — Kevin T Truong
*Assistant Examiner* — Michael Araj
(74) *Attorney, Agent, or Firm* — Lerner, David, Littenberg, Krumholz & Mentlik, LLP

(57) ABSTRACT

A screwdriver for bone screws, especially for compression screws and locking screws, has a handle and shaft extending out centrally from the handle. The shaft has a screwdriving tool on its free end. The shaft, includes a flexible shaft portion, wherein the shaft has two rigid, solid portions on both sides of the flexible portion. The flexible shaft portion has a flexible element for the transmission of a torque, and at least the flexible shaft portion is surrounded by an elastic protection hose or a rubber or plastic elastomeric tubular cover.

20 Claims, 1 Drawing Sheet

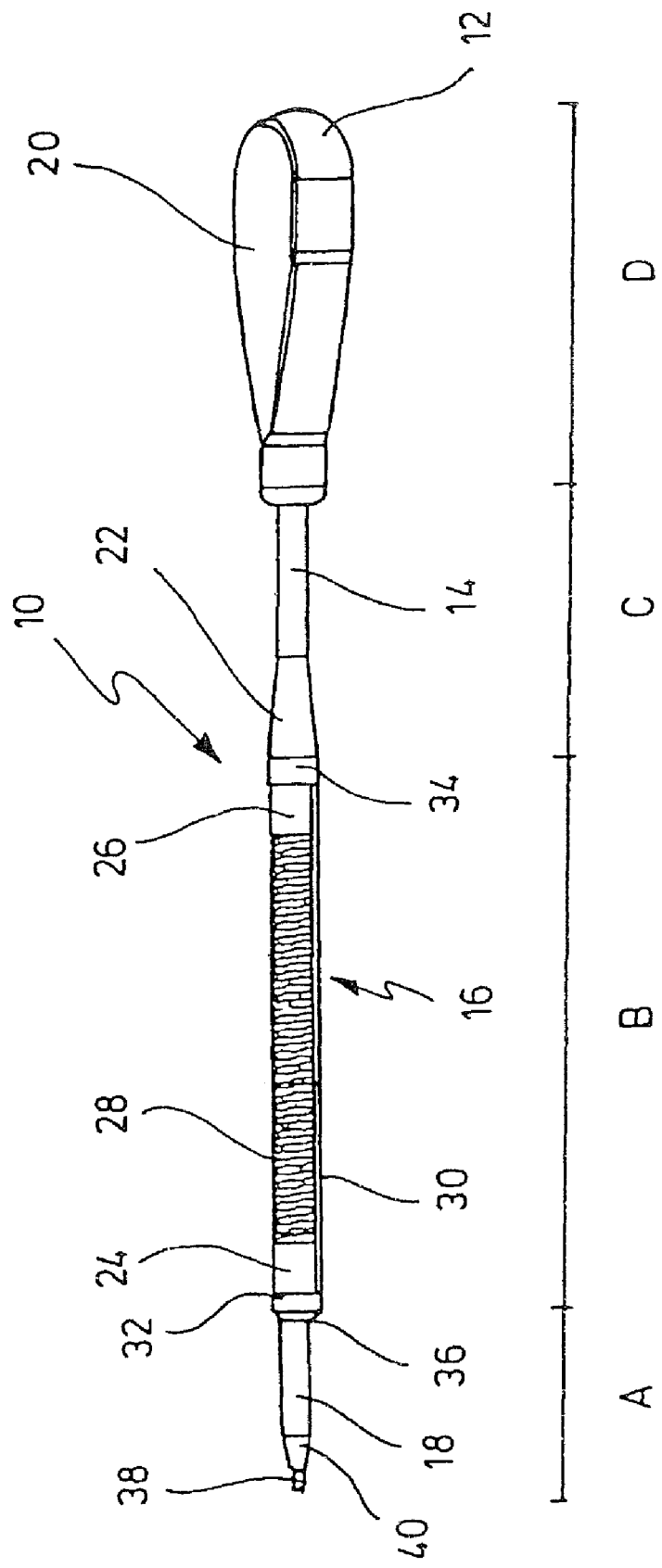

SCREWDRIVER FOR BONE SCREWS

CROSS-REFERENCE TO RELATED APPLICATION

This application is a continuation of U.S. application Ser. No. 10/990,243, filed on Nov. 16, 2004, the disclosure of which is incorporated herein by reference.

BACKGROUND OF THE INVENTION

The present invention relates to a screwdriver for bone screws, especially for compression screws and locking screws on a bone nail. More particularly the invention relates to a flexible screw driver for use in surgery.

From DD 238 724 A1, a medical screwdriver is known, which embraces a screw head with positive and non-positive fit.

From DE 101 18 570 A1, a surgical drill is known, the shaft of which has a central longitudinal bore for a fibre-optical position transmitting device. The shaft of the drill has a clutch, upon which a drill head can be placed, a flexible shaft portion made from coiled spring steel directly adjoining to the clutch and a rigid shaft portion connected to the flexible shaft portion. A longitudinal continuous bore extends through the shaft with the rigid and the flexible shaft portions, into which bore a position transmitting device is introduced. Further, in DE 101 18 570 A1 it is proposed to insert a screwdriver or another tool into the clutch. With this drill, it has proven to be disadvantageous because it is hard to manipulate, especially when used as a screwdriver, and that it is difficult to clean after using thus requiring considerable expenditure of work.

SUMMARY OF THE INVENTION

The invention has as one aspect to create a screwdriver which avoids the aforementioned disadvantages and which allows safe operation by the surgeon.

According to the invention, this aspect is provided for by a screwdriver for bone screws, especially for compression and locking screws, having a handle, a shaft extending out from the handle, which shaft has a screw driving or other tool at a free end thereof. The shaft has a flexible portion and two rigid portions on either side of the flexible portion. The flexible shaft portion has a flexible element for transmitting torque. At least the flexible shaft portion is surrounded by an elastic protective hose or elastomeric sheath. The flexible shaft portion has a holding portion on each of its ends, respectively, the flexible element being held between the holding portions. Normally, the holding portions are solid. Preferably, the flexible element consists of a coiled wire, however, various other flexible shaft designs for torque transmission can be used such as a tube. If a tube is used the tube element can be provided with slits which run transverse to the longitudinal direction. The hose or sheath preferably consists of a biocompatible material such as silicone rubber. Preferably the diameter of the shaft in the flexible area is larger than the rigid shaft portions. The diameter of the connecting shaft between the handle and the flexible portion may have a diameter which increases moving towards the flexible portion in a conical form. Likewise, the shaft between the tool at the free end of the screwdriver or other instrument and the flexible region tapers towards the tool on the conical form. While the handle preferably is essentially circular, it may have a flattened side with the flattened side indicating a known orientation of the tool. Preferably, the flexible portion has a length which is less than half ($\frac{1}{2}$) but greater than one third ($\frac{1}{3}$) the total length of the instrument, i.e. between $\frac{1}{2}$ and $\frac{1}{3}$ of the length from the top of the handle to the free end of the instrument. The sheath may be rubber, plastic, or other elastomeric materials and may have a diameter of approximately 10 mm and a thickness of approximately 2 mm.

The screwdriver according to the invention is provided for bone screws, especially for compression screws and locking screws on bone nails. The screwdriver has a preferably longitudinal handle, with a shaft centrally extending out from the handle. A screw driving tool is provided on the free end thereof to match the drive on the screw. The shaft has a flexible shaft portion. According to a preferred embodiment of the invention, the shaft has two rigid portions provided on both sides of the flexible shaft portion. Preferably, the flexible shaft portion has on each of its two ends one holding portion, respectively, and a flexible element held between them. Preferably, the flexible element consists of a flexible tube element or of a helically coiled wire. At least the flexible shaft portion is surrounded by an elastic protection tubular cover or hose. The arrangement of the flexible shaft portion between two rigid shaft portions allows for a safe and precise handling, the surgeon having good control over the torque exerted. The flexible shaft portion with a flexible element creates the possibility for continuous bending of the shaft. The elastic protection hose, arranged at least across the elastic shaft portion, prevents the intrusion of blood and tissue into the flexible shaft portion and thus facilitates cleaning and disinfection of the screwdriver after use.

In the preferred embodiment of the flexible element as a flexible tube element, the latter is preferably formed by a metal tube, the outer wall of which presents slits which extend transversely to the longitudinal direction. Preferably, the protection hose consists of a biocompatible material, silicone being particularly suited.

In a preferred embodiment, the diameter of the shaft is larger in its flexible portion than in the rigid portions.

The cross section of the shaft, between handle and flexible portion, increases towards the flexible portion in a conical form. Also, the cross section of the shaft between tool and flexible portion may taper towards the tool in a conical form.

In one preferred embodiment, the handle with an essentially circular cross section has one flattened side, the flattened side indicating the orientation of the screwdriver or other tool. Through this, the surgeon operating the screwdriver can obtain an impression of the orientation of the tool, even when the tool point is not visible or only partly visible.

For better handling of the screwdriver, it has proven to be particularly advantageous that the flexible portion has a length which accounts for less than half of the total length. Preferably, the length of the flexible portion with respect to the total length is longer than one third of the total length, however.

In the preferred embodiment, the rigid shaft portion with the screwdriver tool is shorter than the second rigid shaft portion.

In a preferred construction, the screwdriver tool is formed in one piece on the free end of the rigid shaft portion. The tool, of course, could be modular. In a functional construction, the holding portions and the flexible element have a diameter of approximately 10 cm, the hose having preferably a wall thickness of approximately 2 mm.

BRIEF DESCRIPTION OF THE DRAWINGS

The present invention will be better understood on reading the following detailed description of non-limiting embodiments thereof, and on examining the accompanying drawing, in which:

FIG. 1 is an elevation view of one preferred embodiment of the screwdriver according to the invention is hereinafter explained in more detail by means of the FIGURE.

DETAILED DESCRIPTION

The single FIGURE shows a medical screwdriver 10, with a handle 12, a first rigid shaft portion 14, a flexible shaft portion 16 and a second rigid shaft portion 18. The handle 12 has a flattened side 20, which extends along the longitudinal axis of the shaft. The rigid and massively realised, preferably solid, shaft portion 14 juts out of the handle 12, the diameter of which increases conically upon the transition to the flexible portion 16 in a region 22.

The flexible portion 16 has on its two ends one holding portion 24 and 26, respectively, between which a helically coiled wire, from spring steel e.g., is held. A protective hose 30 of elastic, biocompatible material is drawn on the portions 24 and 26 as well as over the flexible wire. In the represented preferred example, the protective hose is a hose from silicone material, having a wall thickness of approximately 2 mm.

Besides the represented variant, in which the flexible region 28 is made from a helically coiled wire, it is also possible to form the flexible region by a thin-walled metal tube, the outer wall of which is interrupted by slits standing transversely to the longitudinal axis, through which bending of the metal tube becomes possible. For example, see U.S. Pat. Nos. 6,337,142 and 6,416,517 the teachings of which are incorporated herein by reference. Alternatively, thin-walled profiled metal tubes may be used to create the flexible portion 16. When using a metal tube, it is important that an almost continuous bending can take place within a predetermined range of angles.

The protection hose 30 preferably terminates on the shaft on its two ends flush with the outer walls 32 and 34.

The rigid portion 18 adjoins to a conical portion 36 adjacent to the flexible region 16. The tool tip 38 is formed on the rigid portion 18 and verges via a region 40, which also enlarges conically, into the rigid region 18.

The total length of the screwdriver according to the invention is composed of the length A of the rigid portion 18, the length B of the flexible portion 16, the length C of the rigid portion 14, and the length D of the handle 12. The length proportions are herein selected such that the rigid portion 18 with its length A is shorter than the rigid portion 14 with its length C (A<C). The flexible portion 16 with its length B is longer than each of the rigid portions and the handle (B>A, B>C, B>D). With respect to the total length (A+B+C+D), the flexible portion 16 has a length B which is smaller than half the total length (2B<A+B+C+D) and larger than one third of the total length (3B>A+B+C+D).

The represented screwdriver with flexible shaft is particularly suited for the driving of screws which are disposed on a bone nail, like compression or locking screws, e.g. The particular advantage is that the driving of the screw by hand does not have to proceed in a straight-lined prolongation of the screw axis. Thus, this prevents the space for the screwdriver handle from being blocked by the patient's body, as is the case by the iliac wing upon the anterograde access in the femur.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
a handle at a first end and a screw driving tool portion at a second end the handle extending along a longitudinal axis, a shaft extending between the first and second ends of the instrument;
a flexible shaft portion extending at least partially between first and second rigid holding portions of the shaft formed on either side of the flexible shaft portion; and
a flexible elastomeric cover having an outer diameter annularly disposed around said flexible shaft portion and extending longitudinally over the length of the flexible shaft portion and over at least a first portion of the first and second rigid holding portions disposed on respective sides of the flexible shaft portion, an end portion of each of the first and second rigid holding portions spaced from the flexible shaft portion, each end portion having an outer diameter greater than an outer diameter of the first portions of the first and second rigid holding portions, wherein the handle has an essentially circular diameter with a planar surface extending between two circular outer side surfaces, the planar surface extending parallel to the handle axis, the planar surface indicating the orientation of the screw-driving tool portion.

2. The surgical instrument set forth in claim 1, wherein the flexible shaft portion has a length which accounts for less than half of a total length of the screw-driving tool portion.

3. The surgical instrument as set forth in claim 2 wherein the flexible shaft portion has a length greater than one third of the total length of the screw-driving tool portion.

4. The surgical instrument as set forth in claim 1 wherein said elastomeric cover is made of silicone rubber.

5. A screwdriver for bone screws, especially for compression screws and locking screws, comprising:
a handle;
a shaft extending out from the handle, which has a screw-driving tool on an end thereof;
the shaft having a flexible shaft portion, said shaft has first and second rigid holding portions on respective sides of the flexible shaft portion each rigid holding portion having an end part spaced from the flexible shaft portion and a part adjacent respective sides of the flexible shaft portion, the end part spaced from the flexible shaft portion having an outer diameter greater than an outer diameter of the part of each of the rigid holding portions adjacent the flexible shaft portion;
the flexible shaft portion has a flexible element for the transmission of a torque; and
an elastomeric protection hose annularly disposed around the flexible shaft portion and extending longitudinally over the length of the flexible shaft portion and over the part of each of the first and second rigid holding portions disposed adjacent the respective sides of the flexible shaft portion, the elastomeric protection hose having an outer diameter equal to the outer diameter of each of the end parts of the first and second rigid holding portions, so that the elastomeric protection hose terminates flush with the outer diameter of each end part;
wherein the flexible shaft portion has a length which is approximately ⅓ of the length of the screwdriver, at least a major part of the flexible shaft portion being arranged in a front half of the screwdriver.

6. The screwdriver according to claim 5, wherein the flexible element consist of a helically coiled wire.

7. The screwdriver according to claim 5, wherein the flexible element consist of a flexible tube element.

8. The screwdriver according to claim 7, wherein the flexible tube element is provided with slits, which run transversely to the longitudinal direction.

9. The screwdriver according to claim 5, wherein the protection hose consists of a biocompatible material, particularly of silicone.

10. The screwdriver according to claim 5, wherein the shaft has first and second rigid portions adjacent the first and second rigid holding portions, the diameter of the shaft in the flexible shaft portion is larger than in the rigid shaft portions.

11. The screwdriver according to claim 10, wherein the diameter of the second rigid shaft portion between the handle and the flexible shaft portion increases towards the flexible shaft portion in a conical form.

12. The screwdriver according to claim 10, wherein the diameter of the first rigid shaft portion between the screwdriver and the flexible shaft portions tapers towards the tool in a conical form.

13. The screwdriver according to claim 10, wherein the first rigid portion of the shaft is shorter than the second rigid holding portion.

14. The screwdriver according to claim 5, wherein the handle has an essentially circular diameter with a flattened side, the flattened side indicating the orientation of the screw-driving tool.

15. The screwdriver according to claim 5, wherein the flexible shaft portion has a length which accounts for less than half of a total length of the screwdriver (A+B+C+D).

16. The screwdriver according to claim 5, wherein the flexible shaft portion has a length which accounts for more than one third of a total length of the screwdriver (A+C+B+D).

17. The screwdriver according to claim 16, wherein the first and second rigid holding portions and the elastomeric hose have a diameter of approximately 10 mm.

18. The screwdriver according to claim 5, wherein the screw-driving tool is formed in one piece on a free end of the first rigid holding portion.

19. The screwdriver according to claim 5, wherein the elastomeric protection hose has a wall thickness of approximately 2 mm.

20. A surgical instrument comprising:
a handle at a first end and a tool portion at a second end;
a flexible shaft portion extending at least partially between first and second rigid holding portions, each rigid holding portion formed from a body having an outer first diameter portion and a second smaller diameter portion;
a flexible elastomeric cover having an outer diameter annularly disposed around said flexible shaft and extending longitudinally over the length of the flexible shaft portion and over the second portion of the first and second rigid holding portions disposed on respective sides of the flexible shaft portion, the outer first diameter portion of each the first and second rigid holding portions spaced from the flexible shaft portion having an outer diameter greater than the outer diameter of the second smaller diameter portion of the first and second rigid holding portions, thereby forming a step, the outer diameter of the outer first diameter portion equal to the outer diameter of the flexible elastomeric cover, so that the flexible elastomeric cover hose terminates flush with the outer diameter of the outer first diameter portion;
wherein the flexible shaft portion has a length which is approximately ⅓ of the length of the instrument, at least a major part of the flexible shaft portion being arranged in a front half of the instrument.

* * * * *